(12) United States Patent
Di Luccio et al.

(10) Patent No.: US 7,196,026 B2
(45) Date of Patent: Mar. 27, 2007

(54) FIBERS PROVIDING CONTROLLED ACTIVE AGENT DELIVERY

(75) Inventors: Robert Cosmo Di Luccio, Alpharetta, GA (US); Frank Jerrel Akin, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/600,301

(22) Filed: Jun. 20, 2003

(65) Prior Publication Data

US 2004/0082239 A1 Apr. 29, 2004

Related U.S. Application Data

(62) Division of application No. 09/716,665, filed on Nov. 20, 2000, now abandoned.

(60) Provisional application No. 60/173,193, filed on Dec. 27, 1999.

(51) Int. Cl.
*D04H 1/00* (2006.01)
*D04H 13/00* (2006.01)
*D04H 3/00* (2006.01)
*D04H 5/00* (2006.01)

(52) U.S. Cl. ............ 442/361; 442/123; 442/364; 442/400; 442/401; 442/409; 428/364; 428/365; 428/373; 428/374

(58) Field of Classification Search .......... 442/123, 442/361, 364, 400, 401, 409; 428/364, 365, 428/373, 374
See application file for complete search history.

(56) References Cited

U.S. PATENT DOCUMENTS

| | | | |
|---|---|---|---|
| 3,312,758 A | 4/1967 | Lowes, Jr. ............ | 260/895 |
| 3,338,992 A | 8/1967 | Kinney ............. | 264/24 |
| 3,341,394 A | 9/1967 | Kinney ............. | 161/72 |
| 3,423,266 A | 1/1969 | Davies et al. ......... | 156/167 |
| 3,502,538 A | 3/1970 | Petersen ............ | 161/150 |
| 3,502,763 A | 3/1970 | Hartmann ............ | 264/210 |
| 3,542,615 A | 11/1970 | Dobo et al. .......... | 156/181 |
| 3,692,618 A | 9/1972 | Dorschner et al. ....... | 161/72 |

(Continued)

FOREIGN PATENT DOCUMENTS

| | | |
|---|---|---|
| EP | 0 499 181 | 8/1992 |
| EP | 0 668 083 | 8/1995 |
| JP | 61083316 A * | 4/1986 |
| JP | 61 296118 | 12/1986 |
| WO | 98/20190 | 5/1998 |

OTHER PUBLICATIONS

*Polymer Blends and Composites* by John A. Manson and Leslie H. Sperling, copyright 1976 by Plenum Press, a division of Plenum Publishing Corporation of New York, IBSN 0-306-30831-2, at pp. 273 through 277.

Primary Examiner—Norca L. Torres-Velazquez
(74) Attorney, Agent, or Firm—Dority & Manning, P.A.

(57) ABSTRACT

An agend fiber composed of an active agent/positive dispensing carrier combination and a fiber forming component. As a fiber or nonwoven or textile fabric containing the fiber, the agend delivers the active agent at a desired rate under conditions of use. Product applications include personal care products such as diapers, training pants, swimwear, refastenable pants, absorbent underwear, feminine hygiene products, incontinent wear, wound dressings and cleansing wipes. The fibers may be formed as monocomponent fibers or multicomponent fibers of varying configurations. Active agents that can be dispensed include skin wellness agents, therapeutic agents, and cleaning agents, for example. In accordance with the invention, agend fibers provide desirable uniformity of dispensing and control of dispensing rates.

20 Claims, 3 Drawing Sheets

U.S. PATENT DOCUMENTS

| | | | |
|---|---|---|---|
| 3,802,817 A | 4/1974 | Matsuki et al. | 425/66 |
| 3,849,241 A | 11/1974 | Butin et al. | 161/169 |
| 3,939,836 A * | 2/1976 | Tunc | 128/284 |
| 4,070,218 A | 1/1978 | Weber | 156/167 |
| 4,340,563 A | 7/1982 | Appel et al. | 264/518 |
| 4,853,281 A | 8/1989 | Win et al. | 428/286 |
| 4,923,914 A * | 5/1990 | Nohr et al. | 524/99 |
| 4,965,128 A | 10/1990 | Greidanus et al. | 428/398 |
| 5,108,820 A | 4/1992 | Kaneko et al. | 428/198 |
| 5,108,827 A | 4/1992 | Gessner | 428/219 |
| 5,336,552 A | 8/1994 | Strack et al. | 428/224 |
| 5,382,400 A | 1/1995 | Pike et al. | 264/168 |
| 5,418,045 A | 5/1995 | Pike et al. | 428/198 |
| 5,456,982 A * | 10/1995 | Hansen et al. | 428/370 |
| 5,534,335 A | 7/1996 | Everhart et al. | 428/224 |
| 5,593,682 A | 1/1997 | Papas et al. | 424/401 |
| 5,605,749 A | 2/1997 | Pike et al. | 442/60 |
| 5,609,587 A | 3/1997 | Roe | 604/360 |
| 5,770,528 A * | 6/1998 | Mumick et al. | 442/59 |
| 5,866,488 A | 2/1999 | Terada et al. | 442/362 |
| 5,895,710 A | 4/1999 | Sasse et al. | 442/334 |
| 5,935,883 A | 8/1999 | Pike | 442/340 |
| 6,120,803 A * | 9/2000 | Wong et al. | 424/473 |
| 6,162,537 A * | 12/2000 | Martin et al. | 428/373 |
| 6,723,428 B1 * | 4/2004 | Foss et al. | 428/370 |

\* cited by examiner

FIBERS PROVIDING CONTROLLED ACTIVE AGENT DELIVERY

This application is a divisional of 09/716,665 filed Nov. 20, 2000; now abandoned which claims benefit to U.S. Provisional Application No. 60/173,193 filed Dec. 27, 1999.

FIELD OF THE INVENTION

The present invention is directed to multicomponent fibers that include at least one component that provides and maintains fiber properties under conditions of intended use and at least one agend (as defined below) component that contains an agent within an extrudable positive displacement carrier composition and dispenses the agent under conditions of intended use. When formed into a nonwoven fabric, a textile, or a batt, the fibers provide a wide degree of control over the rate and uniformity of delivery of the agent under conditions of intended use. Contemplated applications include as an element of personal care products such as disposable diapers delivering skin care agents, as an element of wound care products delivering therapeutic agents, and as a wipe delivering disinfecting, astringent, anesthetics or cleansing agents.

BACKGROUND

Fibrous substrates used to deliver widely varying agents are well known and readily available for many purposes. Examples include wet wipes, polishing rags, disinfecting bandages, insect repellent wipes and cleaning implements. It is also known to include agents in personal care products such as disposable diapers and the like to improve conditions in skin contact areas. Examples of such products are described in greater detail in U.S. Pat. Nos. 5,609,587 and 5,593,682. Multicomponent fibers are, similarly, known and commercially available for diverse uses. For example, binder bicomponent fibers where one component has adhesive properties under bonding conditions are widely employed to provide integrity to fibrous batts used as absorbents in personal care products or in filter products. Examples of such multicomponent fibers are described in U.S. Pat. Nos. 5,382,400 and 5,866,488. Moreover, the incorporation of additives such as surfactants into extrudable polymer compositions and the blooming of such additives to the fiber surface over time are taught by, for example, U.S. Pat. No. 4,070,218.

There remains a need for fibers and webs that can more effectively and efficiently deliver active agents in a uniform and controlled manner. The present invention addresses this need.

SUMMARY OF THE INVENTION

The present invention provides an active agent containing fiber made up of at least one fiber forming component that maintains fiber properties under conditions of intended use and at least one agend agent delivery component containing a positive displacement carrier that dispenses an agent in a controlled manner under conditions of intended use by blooming the agent to the component surface or allowing the component to diffuse out of the carrier under the control of the carrier or pores in the carrier. As a result, the amount of agent required may be minimized, and the gradual dispensing by the blooming or diffusing step extends the useful life of the product.

Multicomponent fibers in accordance with the invention may be formed by coextrusion as sheath/core, side-by-side, islands in the sea, or other multicomponent fiber forming steps known to those of skill in this art. In the form of a nonwoven web containing such multicomponent fibers or monocomponent fibers, the invention provides components of personal care products that dispense skin friendly agents to the wearer's skin in use and aid in producing a skin friendly environment. Agents of particular use for such applications include lotions, creams, or waxes in an alloy composition containing, for example, as a positive displacement carrier, polyvinylpyrrolidone. Other water-soluble polymers such as polyvinyl alcohol, polyethylene glycol, tetramethylene ether glycol, hydroxypropyl methylcellulose may also be used. For skin cleansing applications, active agents such as a diverse set of cosmetically accepted ingredients such as those found in guidebooks such as *International Cosmetic Ingredient Dictionary and Handbook*, Eighth edition and prior editions from CTFA (the Cosmetic, Toiletry, and Fragrance Association) can be used, for example, and for wound care applications, active agents such as topical anesthetics including compounds like benzocaine, benzyl alcohol, butacaine, clove oil, dibucaine, diclonine hydrochloride, eugenol, lidocaine, pramoxine hydrochloride, proparacaine hydrochloride, tetracaine can be used, for example. While the amount of active agent will vary widely depending on the intended use, the efficient and controlled dispensing obtained using the fibers of the present invention allows generally equivalent or better results with less agent when compared with standard coating or impregnating processes.

DETAILED DESCRIPTION

Figure 1:
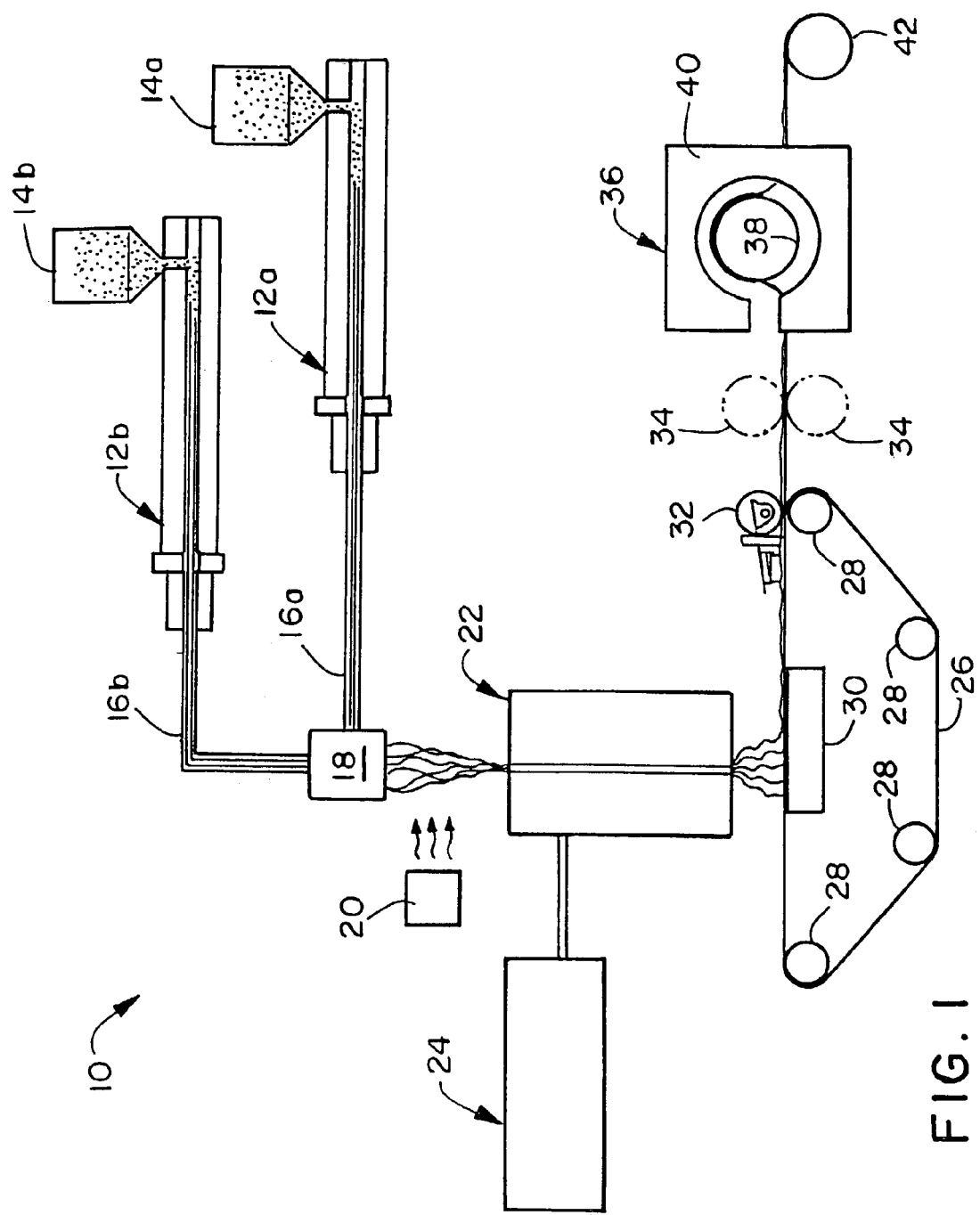
FIG. 1 is a schematic illustration of a method of making the multicomponent fibers of the invention and webs formed therefrom.

While the invention will be described in connection with preferred and other embodiments, it will be understood that it is not intended to limit the invention to those embodiments. On the contrary, it is intended to cover all alternatives, modifications and equivalents as may be included within the spirit and scope of the invention as defined by the appended claims.

DEFINITIONS

As used herein the term "comprising" is open and includes not only recited elements, components or steps but also any additional elements, components or steps that do not prevent operation of the invention as described.

As used herein the term "nonwoven fabric or web" means a web having a structure of individual fibers or threads that are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91). The term "textile" embraces other webs formed, for example, by weaving or knitting.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Levy, and U.S. Pat. No. 3,542,615 to Dobo et al. Spunbond fibers are generally not tacky when they are deposited onto a collecting surface. Spunbond fibers are generally continuous and have diameters larger than 7 microns, frequently, between about 10 and 20 microns.

As used herein the term "meltblown fibers" means fibers formed by extruding a molten thermoplastic material through a plurality of fine, usually circular, die capillaries as molten threads or filaments into converging high velocity gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin. Meltblown fibers are microfibers that may be continuous or discontinuous, are generally smaller than 10 microns in diameter, and are generally tacky when deposited onto a collecting surface.

As used herein, the term "wet-spun" fibers means those formed by extruding a solvent based polymer through a plurality of fine usually circular die capillaries as a series of viscous solutions that are extruded above or in contact with a coagulant solvent to cause exchange of the solvent used to dissolve the polymer. After the solvent exchange, the fibers are carried by either allowing them to collect in a piddle bucket or are drawn by conventional means to further treatment baths or gaseous environments to set up their structure. Such a process is disclosed in U.S. Pat. No. 4,965,128, incorporated herein in its entirety by reference.

As used herein, the term "dry-spun" fibers means those formed by extruding a solvent based polymer through a plurality of fine die capillaries as a series of viscous solutions that are extruded into a column containing a hot gas to cause the solvent to flash off and isolate the polymer. After solvent exchange, the fibers are carried by mechanical means to further treatment baths or gaseous environments to set up their structure. Such a process is also disclosed in U.S. Pat. No. 4,965,128.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configuration of the material. These configurations include, but are not limited to isotactic, syndiotactic and random symmetries.

As used herein the term "monocomponent" fiber refers to a fiber formed from one or more extruders using only one polymer extrudate. This is not meant to exclude fibers formed from one polymer to which small amounts of additives have been added for color, anti-static properties, lubrication, hydrophilicity, etc. These additives, e.g. titanium dioxide for color, are generally present in an amount less than 5 weight percent and more typically about 2 weight percent.

As used herein the term "multicomponent fibers" refers to fibers which have been formed from at least two polymers extrudates extruded from separate extruders but spun together to form one fiber. Multicomponent fibers are also sometimes referred to as conjugate or bicomponent fibers. The polymers are usually different from each other though multicomponent fibers may use the same polymer for different components. The polymers are arranged in substantially constantly positioned distinct zones across the cross-section of the conjugate fibers and extend continuously along the length of the multicomponent fibers. The configuration of such a multicomponent fiber may be, for example, a sheath/core arrangement wherein one polymer is surrounded by another or may be a side by side arrangement or an "islands-in-the-sea" arrangement. Multicomponent fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios.

As used herein the term "biconstituent fibers" refers to fibers that have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

As used herein the term "blend" means a mixture of two or more polymers while the term "alloy" means a sub-class of blends wherein the components are immiscible but have been compatibilized. "Miscibility" and "immiscibility" are defined as blends having negative and positive values, respectively, for the free energy of mixing. Further, "compatibilization" is defined as the process of modifying the interfacial properties of an immiscible polymer blend in order to make an alloy.

As used herein, the term "agend" means a composition containing an active agent and a positive displacement carrier that may, either by itself, or in combination with another component be formed into a fiber by any one or more of the above-described processes. Thus, the agend may form a monocomponent fiber, a multicomponent fiber with one or more other components, or a biconstituent fiber, for example. The amount of active agent in an agend will depend on the agent and the intended use, and the additional positive displacement carrier of the agend will be determined by these factors as well as the ability of the composition as a whole to release the active agent in a controlled manner.

As used herein, the term "personal care product" means diapers, training pants, refastenable pants, absorbent underpants, adult incontinence products, and feminine hygiene products.

As used herein, the term "active agent" means a compound or composition that is capable of forming, by itself or in combination as a blend or mixture with another compound or composition as an agend, an extrudable melt component of a multicomponent fiber, or a component that can be suspended in the spin dope of one or more polymers in a wet or dry spinning process and thereafter being active to produce an intended effect under intended use conditions. In addition, in a combination with the positive displacement carrier, the active agent is capable under use conditions of blooming or diffusing to the surface of the multicomponent fiber in an amount and within a time required to achieve the intended result.

As used herein, the term "positive displacement carrier" means a compound or composition that, when combined with an active agent under conditions of use, will cause the active agent to be dispensed by, for example, diffusing or blooming from the combination at a desired rate.

As used herein the phrase "conditions of use" means the environment expected to be encountered by the fibers or webs of the invention when dispensing of the active agent is desired. Thus for some applications such as bandages it may be body temperature and for others such as wound dressings it may be a combination of temperature and moisture. For cleansing applications a liquid environment may represent conditions of use. Other examples will be readily apparent to those of skill in the art, such as pH changes and the like.

EXAMPLES

For many applications the fiber forming component of the agend fiber of the present invention will be selected from typical thermoplastic polymers such as polyolefins, including polyethylene, polypropylene, copolymers and blends of these, polyesters, including polyethyleneterephthalate, polyamides, including nylons, and various elastomers and plastomers such as polyurethanes and polyesters as are known to those skilled in the art. Because of the experience with these polymers in forming fibers and because they are readily available at low cost, polyolefins will frequently be the choice for the fiber forming component.

For other applications where melt processes are unsuitable, various polymers that can be dissolved in aqueous or nonaqueous solvents can also serve as appropriate positive displacement carriers for agend vehicles and/or fiber forming components. Aqueous based polymer systems such as polyvinyl alcohol, sodium alginate, chitosan, polyvinyl pyrrolidone, hydroxymethyl cellulose and the like could be used as vehicles or non-aqueous based polymer systems such as polyurethane, ethylene vinyl acetate, acrylic based polymers, chitin, ethylcellulose, polyacryonitrile, and the like.

Many examples of active agents will be apparent to those skilled in the art and the selection will depend largely on the intended use. In personal care products with skin contact a number of active agents capable of forming melts is described as vitamin E containing compositions with blends of acytylated monoglyceride and polyoxyethylene fatty acid ester, blends of distilled monoglyceride, distilled propylene glycolmonoester and sodium or calcium stearoyl lactylate; water and oxydized cellulose in U.S. Pat. No. 5,593,682 which is incorporated herein in its entirety by reference. Others specifically for personal care products are described as comprising a liquid polyolpolyester and an immobilizing agent such as a fatty alcohol or paraffin wax in U.S. Pat. No. 5,609,587, also incorporated herein in its entirety by reference. For examples of useful cleansing active agents, such as synthetic oil based waxes and oils, natural agents like beeswax, aqueous dermatological medicaments, germicidal solutions, and perfumes and skin cleansers, for wipes or the like, reference may be had to U.S. Pat. No. 5,605,749 and U.S. Pat. No. 4,853,281, each of which is also incorporated herein in its entirety by reference.

Because active agents will generally be relatively expensive and frequently not capable, by themselves, of forming fibers, they will normally be incorporated into an agend composition as a minor proportion, for example, up to about 5% by weight, and often less in the range of up to about 3% by weight. The major proportion of the composition will be made up of, in most cases, a positive displacement carrier either alone or in a blend or other combination with a thermoplastic polymer that can be extruded with the agend to form a fiber or as a fiber forming component to form a multicomponent fiber. In addition, the positive displacement carrier part of the agend will be selected so as to facilitate blooming or migration of the active agent to the fiber surface in a controlled manner to be available to produce the desired effect under intended use conditions.

Examples of combinations for fiber forming polymers and agend composition positive displacement carriers include water soluble or lipophilic active agents and polymers that can be dissolved in similar or miscible solvents or polymers that are capable of solubilizing the active ingredient. Others will be apparent to those of skill in fiber forming and can be found by reference to patents such as U.S. Pat. No. 5,418,045, for example, which is incorporated herein in its entirety by reference. Other additives such as compatibilizers may be incorporated into either the fiber-forming component or the agend to facilitate the formation of the monocomponent or multicomponent fibers. Examples of such compatibilizers and representative use ranges may be found by reference to U.S. Pat. No. 5,534,335 which is incorporated herein in its entirety by reference.

The agend fibers of the present invention can be formed, for example, using conventional multicomponent fiber forming processes. Referring to FIG. 1, for example, a process line 10 for preparing a preferred embodiment of the present invention is disclosed. The process line 10 is arranged to produce bicomponent continuous filaments, but it should be understood that the present invention comprehends nonwoven fabrics made with monocomponent agend filaments as well as multicomponent filaments having more than two components. For example, the fiber or fabric of the present invention can be made with filaments having three or four components. The process line 10 includes a pair of extruders 12a and 12b for separately extruding a fiber forming polymer component A as described herein and an agend component B. Polymer component A is fed into the respective extruder 12a from a first hopper 14a and component B is fed into the respective extruder 12b from a second hopper 14b. Polymer component A and component B are fed from the extruders 12a and 12b through respective polymer conduits 16a and 16b to a spinneret 18. Spinnerets for extruding bicomponent filaments are well known to those of ordinary skill in the art and thus are not described here in detail. Generally described, the spinneret 18 includes a housing containing a spin pack which includes a plurality of plates stacked one on top of the other with a pattern of openings arranged to create flow paths for directing components A and B separately through the spinneret. The spinneret 18 has openings arranged in one or more rows. The spinneret openings form a downwardly extending curtain of filaments when the polymers are extruded through the spinneret. For the purposes of the present invention, spinneret 18 may be arranged to form side-by-side, sheath/core or islands-in-the-sea bicomponent filaments illustrated in FIGS. 2A, 2B, and 2C as well as modified sheath/core combinations such as in FIG. 3.

The process line 10 also includes quench blower 20 positioned adjacent the curtain of filaments extending from the spinneret 18. Air from the quench air blower 20 quenches the filaments extending from the spinneret 18. The quench air can be directed from one side of the filament curtain as shown in FIG. 1, or both sides of the filament curtain. A fiber draw unit or aspirator 22 is positioned below the spinneret 18 and receives the quenched filaments. Fiber draw units or aspirators for use in melt spinning polymers are well known as discussed above. Suitable fiber draw units for use in the process of the present invention include a linear fiber aspirator of the type shown in U.S. Pat. No. 3,802,817 and eductive guns of the type shown in U.S. Pat. Nos. 3,692,618 and 3,423,266, the disclosures of which are incorporated herein by reference in their entireties. Generally described, the fiber draw unit 22 includes an elongate vertical passage through which the filaments are drawn by aspirating air entering from the sides of the passage and flowing downwardly through the passage. A heater 24 supplies hot aspirating air to the fiber draw unit 22. The hot aspirating air draws the filaments and ambient air through the fiber draw unit. An endless foraminous forming surface 26 is positioned below the fiber draw unit 22 and receives the continuous filaments from the outlet opening of the fiber draw unit. The forming surface 26 travels around guide rollers 28. A vacuum 30 positioned below the forming surface 26 where the filaments are deposited draws the filaments against the forming surface. The process line 10 further includes a compression roller 32 which, along with the forwardmost of the guide rollers 28, receive the web as the web is drawn off of the forming surface 26. In addition, the process line includes a bonding apparatus such as thermal point bonding rollers 34 (shown in phantom) or a through-air bonder 36. Thermal point bonders and through-air bonders are well known to those skilled in the art and are not described here in detail. Generally described, the through-air bonder 36 includes a perforated roller 38, which receives the web, and a hood 40 surrounding the perforated roller. Lastly, the process line 10 includes a winding roll 42 for taking up the finished fabric.

To operate the process line 10, the hoppers 14a and 14b are filled with the respective polymer component A and agend B. Polymer component A and agend B are melted and extruded by the respective extruders 12a and 12b through polymer conduits 16a and 16b and the spinneret 18. Although the temperatures of the molten polymers vary depending on the polymers used, when polypropylene and polyethylene are used as component A and part of agend B respectively, the preferred temperatures of the polymers range from about 370° to about 530° F. and preferably range from 400° to about 450° F. As the extruded filaments extend below the spinneret 18, a stream of air from the quench blower 20 at least partially quenches the filaments and, if desired, may develop a latent helical crimp in the filaments. The quench air preferably flows in a direction substantially perpendicular to the length of the filaments at a temperature of about 45° to about 90° F. and a velocity from about 100 to about 400 feet per minute. After quenching, the filaments are drawn into the vertical passage of the fiber draw unit 22 by a flow of hot air from the heater 24 through the fiber draw unit. The fiber draw unit is preferably positioned 30 to 60 inches below the bottom of the spinneret 18. If crimp is desired, the temperature of the air supplied from the heater 24 is sufficient that, after some cooling due to mixing with cooler ambient air aspirated with the filaments, the air heats the filaments to a temperature required to activate the crimp. The temperature required to activate the crimp of the filaments ranges from about 110° F. to a maximum temperature less than the melting point of the lower melting component which for through-air bonded materials is the second component B. The temperature of the air from the heater 24 and thus the temperature to which the filaments are heated can be varied to achieve different levels of crimp. Generally, a higher air temperature produces a higher number of crimps. The ability to control the degree of crimp of the filaments is a particularly advantageous feature because it allows one to change the resulting density, pore size distribution and drape of the fabric by simply adjusting the temperature of the air in the fiber draw unit. The filaments are deposited through the outlet opening of the fiber draw unit 22 onto the traveling forming surface 26. The vacuum 20 draws the filaments against the forming surface 26 to form an unbonded, nonwoven web of continuous filaments. The web is then lightly compressed by the compression roller 32 and then thermal point bonded by rollers 34 or through-air bonded in the through-air bonder 36. In the through-air bonder 36, air having a temperature above the melting temperature of component B and below the melting temperature of component A is directed from the hood 40, through the web, and into the perforated roller 38. The hot air melts the lower melting polymer component of agend B and thereby forms bonds between the bicomponent filaments to integrate the web. When polypropylene and polyethylene are used as polymer component A and part of agend B respectively, the air flowing through the through-air bonder preferably has a temperature ranging from about 230° to about 280° F. and a velocity from about 100 to about 500 feet per minute. The dwell time of the web in the through-air bonder is preferably less than about 6 seconds. It should be understood, however, that the parameters of the through-air bonder depend on factors such as the type of polymers used and thickness of the web. Lastly, the finished web is wound onto the winding roller 42 and is ready for further treatment or use.

Once the agend fibers are formed, for applications using very fine fibers to advantage, the multicomponent fibers can be treated either mechanically, for example by needling or stretching, or chemically by the use of solvents or the like, to split the fibers into two or more of the individual components. A particular example would be for a wound dressing where it is desired to increase capillary forces drawing wound exudate away from the wound and into the absorbent component of the dressing. Splitting of bicomponent fibers is described, for example, in U.S. Pat. Nos. 5,895,710 and 5,935,883, each of which is incorporated herein in its entirety by reference.

Figure 2A:
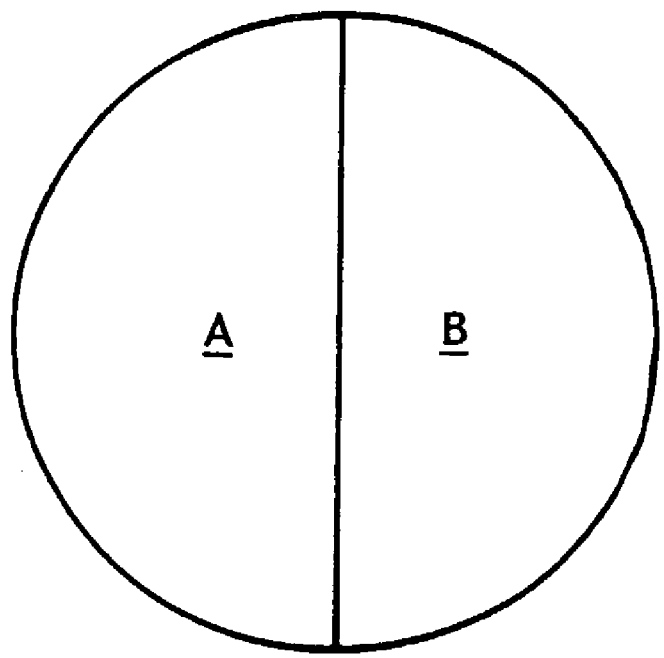
FIGS. 2A, 2B and 2C are schematic cross-sectional views of side-by-side, sheath/core, and islands-in-the-sea multicomponent fibers of the present invention.
Figure 2B:
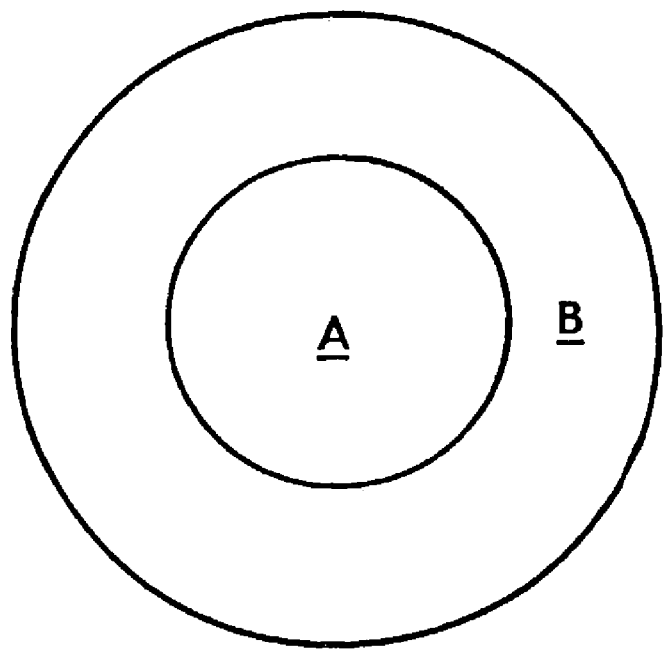
Figure 2C:
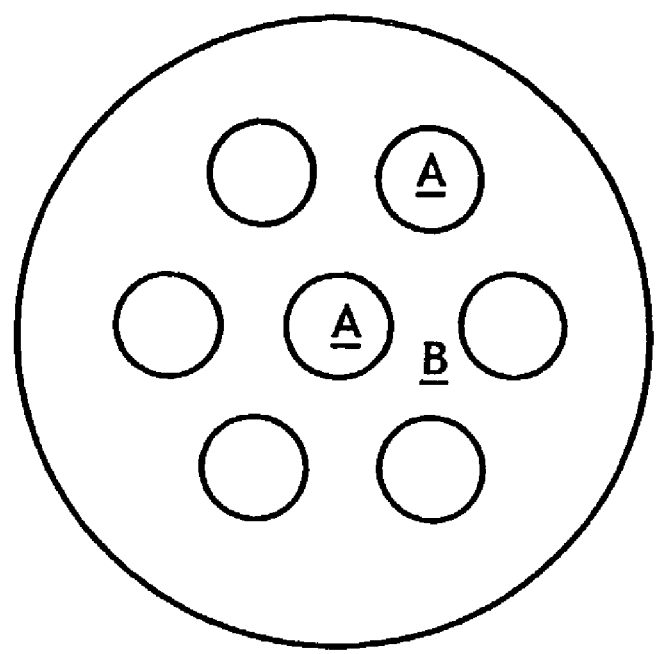

Turning to FIG. 2A, there is shown a side-by-side bicomponent fiber in cross-section showing the distribution of polymer component A and agend component B. FIG. 2B is a similar illustration of a sheath/core bicomponent fiber showing a core of polymer component A and a sheath of agend component B. FIG. 2C is a similar illustration of an islands-in-the-sea bicomponent fiber cross-section. As will be appreciated by those skilled in the art, the components need not be circular and, for example, a star shaped core component can be used to provide increased surface contact between component A and B.

Figure 3:
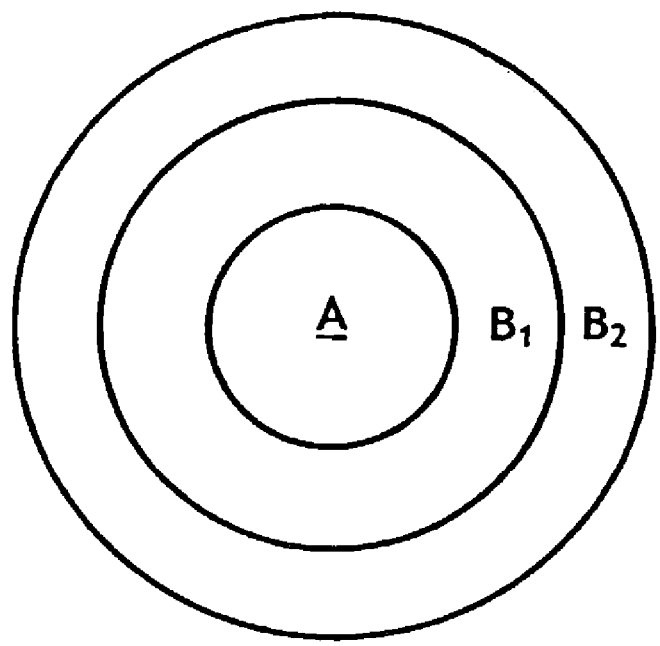
FIG. 3 is a schematic cross-sectional view of an alternative sheath/core multicomponent fiber arrangement.

Referring to FIG. 3, there is shown a cross-section of a multicomponent agend fiber of the present invention having three components in concentric arrangement. Component A can be a fiber-forming polymer component as described above, and components $B_1$ and $B_2$ can be different agends. For example, the outer component, $B_2$, can be a rapid dispensing agend while middle component $B_1$ can be a slower dispensing agend with the result that an extended dispensing period is provided while, at the same time, providing an immediate dosage.

While it is possible to form biconstituent fibers in accordance with the present invention having the polymer component of agend B as the dominant phase, this structure is not preferred because of the difficulty in forming good fiber properties.

As a specific example, the above process was used to form a side-by-side bicomponent spunbond web using sodium alginate as polymer A and an agend composition including as an active agent zinc sulphate monohydrate in positive displacement carrier and polyvinyl pyrrolidone and zinc sulphate monohydrate as the polymer component of agend B. Specific conditions included wet spinning the components in a common aqueous solvent and the web was formed as a coform structure. The resulting nonwoven had a basis weight of 1.0 osy and contained a uniform distribution of the agent on both surfaces. This uniformity was illustrated by analytical measurement. The ability of the web to dispense the agent was demonstrated by solubilization of the active agent in water after which the uniformity was again tested and shown to be present even after an initial dispensing. This clearly shows the advantages of the structure of the present invention.

The above example is representative of the many applications for the present invention which can be readily adapted to dispense other agents including, without limitation, skin friendly compounds like emollients such as lanolin, mineral oil, paraffin, petrolatum, castor oil, coconut oil, glycerin, cetyl alcohol, oleyl alcohol, or isopropyl myristate; repellents for insects, etc. like n-butylacetanilide, diethyltoluamide, ethohexadiol, methyl nonyl ketone; treatments for skin diseases or wounds like agents such as topical anesthetics including compounds like benzocaine, benzyl alcohol, butacaine, clove oil, dibucaine, diclonine hydrochloride, eugenol, lidocaine, pramoxine hydrochloride, proparacaine hydrochloride, tetracaine and the like; waterless and other cleansers like ethyl alcohol green soap, heachlorophene cleansing emulsion, isopropyl alcohol,; cleansers and/or deodorants for hard surfaces like benzalkonium chloride, selenium sulfide, and solium lauryl sulfate; and many others apparent to those skilled in these arts. In fabric and fiber form, the invention provides components for personal care products like disposable diapers, feminine hygiene products, training pants, swimwear, and adult incontinent wear as well as various cleaning implements like wipes, mops, polishing cloths, and so forth. In addition, as a gradual release of an agent is a feature of the invention, applications for wound care and skin rash treatment are primary opportunities for the present invention, especially as the skin contact component of bandages, wraps and the like.

Thus it is apparent that there has been provided, in accordance with the invention, a multicomponent fiber and webs containing multicomponent fibers as well as their use in products that fully satisfy the objectives and advantages set forth in the preceding paragraphs. It is evident that many alternatives, modifications, and variations will be apparent to those skilled in the art in light of the foregoing description. It is intended to embrace all such alternatives, modifications and variations that fall within the scope of the appended claims.

The invention claimed is:

1. A personal care product comprising a nonwoven web, wherein the nonwoven web comprises a multicomponent fiber that is coextruded from at least a first component and a second component, the first component comprising a fiber-forming polymer and the second component comprising an active agent and a positive displacement carrier, wherein the positive displacement carrier comprises a water-soluble polymer and facilitates controlled migration of the active agent to a surface of the fiber.

2. The personal care product of claim 1, wherein the personal care product is selected from the group consisting of diapers, training pants, refastenable pants, absorbent underpants, feminine hygiene products, and adult incontinence products.

3. The personal care product of claim 1, wherein the multicomponent fiber has a sheath/core configuration.

4. The personal care product of claim 3, wherein the multicomponent fiber includes a core comprising the first component and a sheath comprising the second component.

5. The personal care product of claim 3, wherein the multicomponent fiber includes a core comprising the first component, a first sheath comprising the second component, and a second sheath comprising a third component, the third component comprising an active agent and a positive displacement carrier.

6. The personal care product of claim 5, wherein the positive displacement carriers of the second and third components have different active agent dispensing rates.

7. The personal care product of claim 1, wherein the multicomponent fiber has a side-by-side configuration.

8. The personal care product of claim 1, wherein the multicomponent fiber has an islands-in-the-sea configuration.

9. The personal care product of claim 1, wherein the multicomponent fiber is wet spun.

10. The personal care product of claim 1, wherein the multicomponent fiber is dry spun.

11. The personal care product of claim 1, wherein the nonwoven web is a meltblown web, spunbonded web, bonded carded web, or coform web.

12. The personal care product of claim 1, wherein the nonwoven web is a meltblown web.

13. The personal care product of claim 1, wherein the nonwoven web is a spunbonded web.

14. The personal care product of claim 1, wherein the active agent is selected from the group consisting of skin care agents, therapeutic agents, and cleansing agents.

15. The personal care product of claim 1, wherein the active agent is a lotion, cream, or wax.

16. The personal care product of claim 1, wherein the active agent comprises less than about 5% by weight of the second component.

17. The personal care product of claim 1, wherein the active agent comprises less than about 3% by weight of the second component.

18. The personal care product of claim 1, wherein the water-soluble polymer is selected from the group consisting of polyvinyl alcohol, sodium alginate, hydroxypropyl methylcellulose, chitosan, polyethylene glycol, tetramethylene ether glycol, polyvinyl pyrrolidone, and hydroxymethyl cellulose.

19. The personal care product of claim 18, wherein the positive displacement carrier comprises a non-aqueous based polymer system selected from the group consisting of polyurethane, ethylene vinyl acetate, acrylic based polymers, chitin, ethylcellulose, and polyacrylonitrile.

20. The personal care product of claim 1, wherein the first component comprises a fiber-forming polymer selected from the group consisting of polyolefins, polyesters, and nylons.

* * * * *